United States Patent
Murphy et al.

(10) Patent No.: US 7,951,162 B2
(45) Date of Patent: May 31, 2011

(54) DETECTABLE HAND SWITCH AND SURGICAL HANDPIECE

(75) Inventors: John Murdock Murphy, Lausanne (CH); Christian Fleury, Colterd (CH); Laurent Cardoletti, Rennaz (CH); Thierry Bieler, Echichens (CH)

(73) Assignee: Medtronic, Inc., Minneapolis, MN (US)

( * ) Notice: Subject to any disclaimer, the term of this patent is extended or adjusted under 35 U.S.C. 154(b) by 2148 days.

(21) Appl. No.: 10/836,818

(22) Filed: Apr. 30, 2004

(65) Prior Publication Data

US 2005/0245912 A1  Nov. 3, 2005

(51) Int. Cl.
*A61B 17/14* (2006.01)
(52) U.S. Cl. ........................................ 606/176
(58) Field of Classification Search .................... 433/27; 606/167, 170, 171, 176–179, 1; 361/179; 307/116; 327/509; 340/500
See application file for complete search history.

(56) References Cited

U.S. PATENT DOCUMENTS 6,017,354 A * 1/2000 Culp et al. .................... 606/170
6,434,507 B1 * 8/2002 Clayton et al. ............... 702/152

OTHER PUBLICATIONS

Ask Jeeves, "Hall Effect" Apr. 19, 2004, 3 pgs.
Semiconductor Electronics Division, EEEL, Technical Activities, "The Hall Effect", Apr. 19, 2004, 4 pgs.
Ask Jeeves, "SensorsOverview & System Solutions", Apr. 19, 2004, 10 pgs.

* cited by examiner

*Primary Examiner* — Ryan J Severson
(74) *Attorney, Agent, or Firm* — IPLM Group, P.A.

(57) ABSTRACT

A handpiece and system having a surgical handpiece adapted to perform an operation on a patient, the surgical handpiece having a primary circuit being driven by an applied signal. A controller is operatively coupled to supply operating power to the surgical handpiece. A hand switch is operatively coupled in conjunction with the surgical handpiece to at least partially control an operation of the surgical handpiece. The switch has a secondary resonant circuit receiving the applied signal from the primary circuit and couples a response signal back to the primary circuit. Detection circuitry, operatively coupled to primary circuit, is responsive to a characteristic parameter of the response signal indicative of the presence of the hand switch in proximity of the surgical handpiece.

46 Claims, 4 Drawing Sheets

DETECTABLE HAND SWITCH AND SURGICAL HANDPIECE

FIELD OF THE INVENTION

The present invention is related generally to hand switches and surgical handpieces and, more particularly to hand switches detectable by surgical handpieces.

BACKGROUND OF THE INVENTION

Surgical operations commonly employ power tools to perform surgical functions, such as cutting and drilling. Such tools are commonly known as surgical handpieces. The surgical handpieces are held and controlled by the surgeon to aid in surgical techniques.

Surgical handpieces require a power source to operate, usually requiring a particular voltage and a particular current from an electrical power source. Different surgical handpieces have differing voltage and current requirements. Multiple surgical handpieces of different kinds, types and brands are typically available in operating room. It becomes impractical for the operating room to have every kind, type and brand of power supply or control on hand to meet the needs of the multiple kinds, types and brands of surgical handpieces.

Therefore, a single piece of equipment, known as a controller, has been used in operating rooms to control multiple kinds, types and brands of surgical handpieces. Multiple surgical handpieces, typically different surgical handpieces at different times, can all connect to a single controller. The controller can be set or programmed to provide the proper kinds and amounts of electrical power and control signals for each surgical handpiece. This can greatly simplify an operating room.

Some surgeons prefer to use a foot piece, such as a pedal, to control a surgical handpiece. Other surgeons prefer to use a handswitch mounted on the surgical handpiece itself to control a surgical handpiece. Of course, the same surgeon may have a different preference depending upon the particular surgery involved and/or the particular surgical handpiece involved.

Since different types of control, e.g., hand or foot, are available, a controller must know which control the surgeon will use.

A handswitch typically can be removably mounted on a surgical handpiece for hand control. Or the handswitch can be removed from the surgical handpiece for foot control, e.g., by pedal. The controller must know which type of control is being used.

Of course, a switch or program setting on the controller could perform this task. However, an automated system of determining the method of control could simplify the process and eliminate the potential for error by setting a switch to an incorrect position or making an incorrect program setting.

Prior art devices have used magnetic elements, such as a Hall Effect sensor, to sense whether or not a handswitch is attached to a surgical handpiece. Typically, a Hall Effect sensor is located in the surgical handpiece and a magnet is located in the handswitch. The Hall Effect sensor detects the presence of a magnetic field generated by the magnet in the handswitch and signals the controller that a handswitch is present and hand control will be performed.

However, such magnetic sensors are prone to error. The simple presence of a magnetic field in the proximity of the surgical handpiece in the operating room could fool the magnetic sensor into thinking a handswitch was present when it was not present. Of course, there are many pieces of electrical equipment, typically all generating magnetic fields, present in a typical operating room. This could result in erroneous operation of the surgical handpiece. This could result in the surgical handpiece starting or stopping, for example, with potentially disastrous results.

Hall Effect sensors are also prone to degradation over time potentially leading to erratic operation over a period of time. Hence, magnetic sensing of the presence of handswitches on surgical handpieces is prone to error.

Thus, there is a need for equipment to reliably detect the presence of a handswitch on a surgical handpiece.

BRIEF SUMMARY OF THE INVENTION

The present invention positively and unambiguously detect the presence of a handswitch on a surgical handpiece by using an active circuit in the surgical handpiece to drive a resonant circuit in the handswitch. A signal having a characteristic parameter is inductively coupled back to the surgical handpiece. This characteristic parameter can be detected by the surgical handpiece. For example, the resonant circuit will inductively couple back a signal at a particular known frequency. This particular known frequency can be detected in the surgical handpiece to indicate the presence of a handswitch. This technique is much more reliable and safer than merely detecting the presence of a magnetic field.

Further in a preferred embodiment, the amplitude of the signal coupled back to the surgical handpiece can be used to sense the relative position of, e.g., a finger trigger, on the handswitch. A higher amplitude indicates that the resonant circuit is closer to the surgical handpiece. A lower amplitude signal indicates that the resonant circuit is farther away from the surgical handpiece. Thus, the amplitude can be used for a variable control, e.g., a finger control, on the handswitch.

In one embodiment, the present invention provides a system having a surgical handpiece adapted to perform an operation on a patient, the surgical handpiece having a primary circuit being driven by an applied signal. A controller is operatively coupled to supply operating power to the surgical handpiece. A hand switch is operatively coupled in conjunction with the surgical handpiece to at least partially control an operation of the surgical handpiece. The switch has a secondary resonant circuit receiving the applied signal from the primary circuit and couples a response signal back to the primary circuit. Detection circuitry, operatively coupled to primary circuit, is responsive to a characteristic parameter of the response signal indicative of the presence of the hand switch in proximity of the surgical handpiece.

In another embodiment, the present invention provides a system having a surgical handpiece adapted to perform an operation on a patient, the surgical handpiece having a primary circuit being driven by an applied signal. A controller is operatively coupled to supply operating power to the surgical handpiece. A hand switch is operated by finger control of an operator and is operatively coupled in conjunction with the surgical handpiece to at least partially control an operation of the surgical handpiece. The switch has a secondary resonant circuit receiving the applied signal from the primary circuit and inductively couples a response signal back to the primary circuit. Detection circuitry, operatively coupled to primary circuit, is responsive to a characteristic parameter of the response signal indicative of the presence of the hand switch in proximity of the surgical handpiece. The detection circuitry detects a position of the hand switch based, at least in part, as a function of the amplitude of the response signal.

In another embodiment, the present invention provides a surgical handpiece having an operable tool adapted to perform an operation on a patient. A primary circuit is driven by an applied signal. A hand switch is operatively coupled in conjunction with the tool to at least partially control an operation of the tool. The switch has a secondary resonant circuit receiving the applied signal from the primary circuit and couples a response signal back to the primary circuit. Detection circuitry, operatively coupled to primary circuit, is responsive to a characteristic parameter of the response signal indicative of the presence of the hand switch in proximity of the tool.

In another embodiment, the present invention provides a surgical handpiece having an operable tool adapted to perform an operation on a patient. A primary circuit is driven by an applied signal. A hand switch is operatively coupled in conjunction with the tool to at least partially control an operation of the tool. The switch has a secondary resonant circuit receiving the applied signal from the primary circuit and couples a response signal back to the primary circuit. Thus, a characteristic parameter of the response signal may be indicative of the presence of the hand switch in proximity of the tool.

In another embodiment, the present invention provides a method of controlling a surgical handpiece having a primary circuit. The surgical handpiece is adapted to perform an operation on a patient in cooperation with a hand switch having a secondary resonant circuit adapted to at least partially control an operation of the surgical handpiece. The primary circuit is driven with an applied signal. A characteristic parameter of the response signal is detected and coupled back to the primary circuit from the secondary resonant circuit, indicative of the presence of the hand switch in proximity of the surgical handpiece.

In a preferred embodiment, the applied signal is inductively coupled from the secondary resonant circuit back to the primary circuit.

In a preferred embodiment, the detection circuitry detects a position of the hand switch based, at least in part, as a function of the amplitude of the response signal.

In a preferred embodiment, the characteristic parameter of the response signal is a frequency of the response signal.

In a preferred embodiment, the characteristic parameter of the response signal is a time constant of the response signal.

In a preferred embodiment, the hand switch activates the surgical handpiece.

In a preferred embodiment, the hand switch has a finger control that modifies an operating characteristic of the surgical handpiece.

In a preferred embodiment, the hand switch is removable from the surgical handpiece.

DETAILED DESCRIPTION OF THE INVENTION

Figure 1:
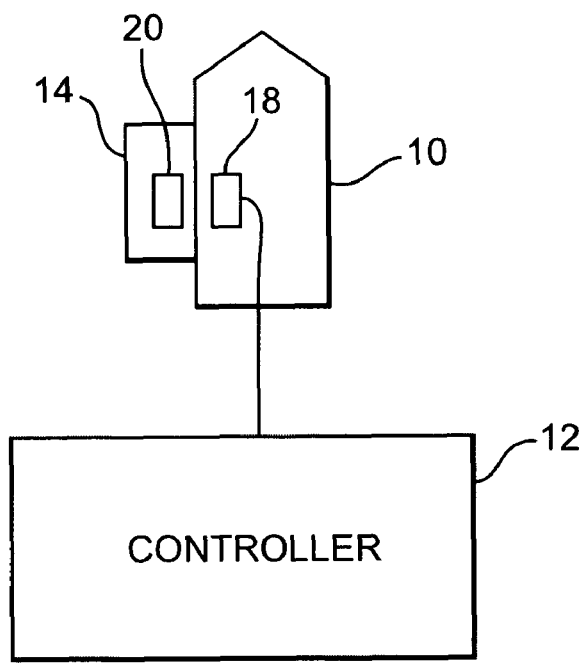
FIG. 1 is a block diagram of a hand switch mounted to a surgical handpiece powered by a controller in accordance with an embodiment of the present invention.
Figure 2:
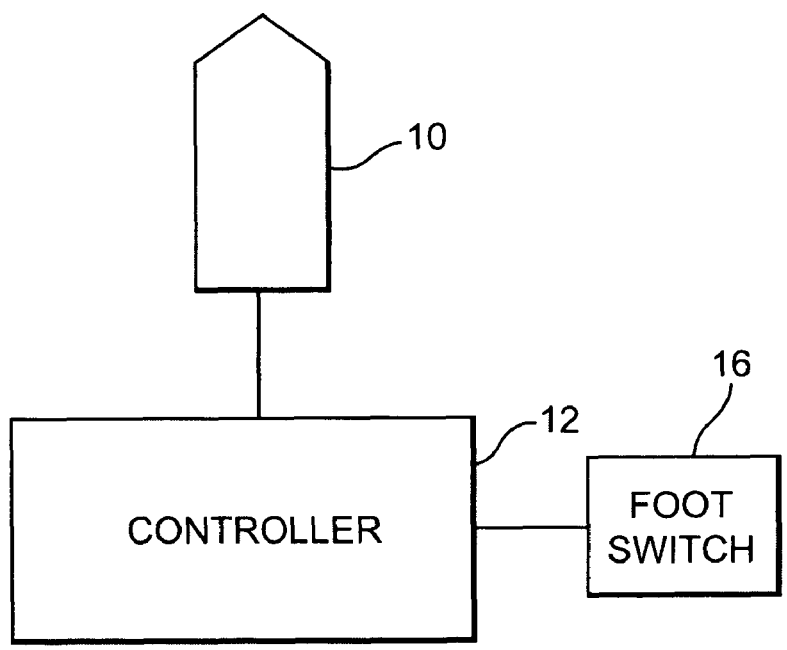
FIG. 2 is a block diagram illustrating a prior surgical handpiece powered by a controller and intended to be controlled, in at least in part, by a foot switch.

FIG. 1 and FIG. 2 illustrate, in block diagram form, two alternative forms of controlling surgical handpiece 10 from controller 12. In FIG. 1, surgical handpiece 10 conventionally connected to controller 12 and surgical handpiece 10 is adapted for hand control denoted by the presence of handswitch 14 mounted on or in conjunction with surgical handpiece 10. Surgical handpiece 10, controller 12 and handswitch 14 are generally all conventional pieces of equipment that are well known in the art. Surgical handpiece 10 can be any of variety surgical handpieces designed to help perform a surgical function such as cutting and/or drilling. Thus, surgical handpiece 10 can be, or can be configured to be, a saw and/or a drill. Saws and drills are provided only as examples and many other types of surgical handpieces 10 are contemplated as well. Controller 12 is also generally convention. Controller 12 operates by providing power to surgical handpiece 10 at the proper voltage and at the proper current and also may provide control signals to surgical handpiece 10. These functions are conventional and do not change with the present invention. Handswitch 14 is also conventional and is conventionally designed to operate with surgical handpiece 10. While these three pieces of equipment are conventional, certain modifications or adjustments need to be made in order to operate in conjunction with the present invention. These modifications will be made apparent below.

FIG. 2 illustrates a prior art surgical handpiece 10 connected to a prior art handswitch 14 for comparison purposes with FIG. 1 only. Foot switch 16 is conventional and is connected conventionally to controller 12 for providing foot control of surgical handpiece 10.

Thus, FIG. 1 illustrates a surgical handpiece 10 having hand control due to the presence of handswitch 14 and FIG. 2 illustrates conventional foot control with foot switch 16.

It may also be possible to have a surgical handpiece 10 which accepts control signals for both a handswitch 14 and a foot switch 16 or another type of control, perhaps a joy stick or trackball. In such a case, the present invention would still be contemplated in determining whether or not to activate handswitch 14 control of surgical handpiece 10.

Referring again to FIG. 1, the present invention can positively and unambiguously detect the presence of handswitch 14 on surgical handpiece 10 by using an active circuit 18 in surgical handpiece 10 to drive resonant circuit 20 in handswitch 14. A signal is applied to active circuit 18 driving active circuit 18. The drive signal for active circuit 18 can come from either surgical handpiece 10, controller 12 or another external piece of equipment. Preferably, drive signal for active circuit 18 is supplied by controller 12. In the presence of resonant circuit 20, a signal having a characteristic parameter is inductively coupled back to surgical handpiece 10. This characteristic parameter can be detected by the surgical handpiece 10 or can be detected by controller 12 or by a completely separate piece of equipment. Preferably, the detection circuit for the characteristic parameter is located in controller 12. For example, resonant circuit 20 will inductively couple back a signal to surgical handpiece 10 at a particular known frequency. This particular known frequency can be detected to indicate the presence of handswitch 14.

Figure 3:
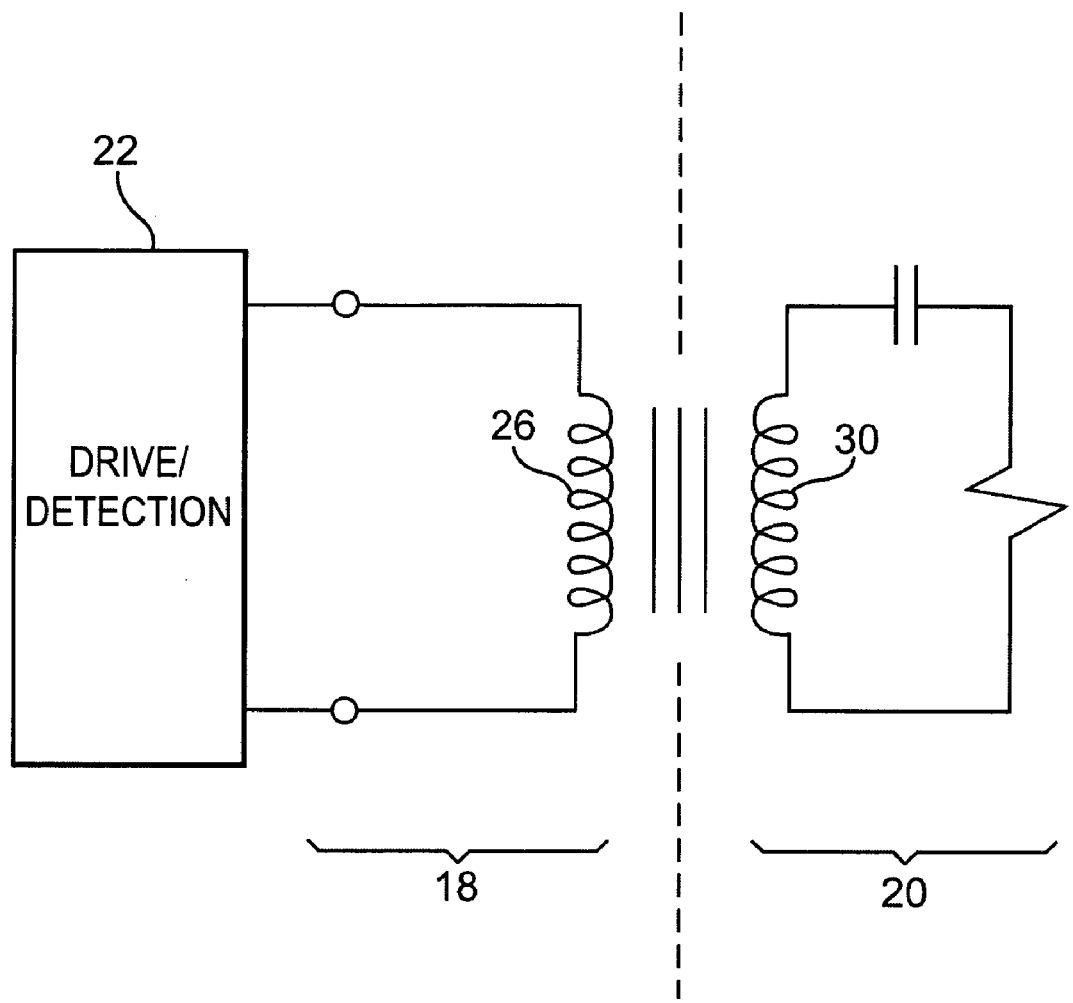
FIG. 3 is a schematic diagram showing operative circuitry in a hand switch and mating surgical handpiece.

FIG. 3 is a schematic diagram of specialized circuitry existing in both surgical handpiece 10 and handswitch 14 to perform identification of presence of handswitch 14. The left side the schematic in FIG. 3 refers to surgical handpiece 10 and the right side of the schematic in FIG. 3 refers to handswitch 14. Drive/detection circuitry 22, which is preferably located in controller 12, supplies an excitation signal 24 (in FIG. 4) to active circuit 18. Active circuit 18 consists of inductor 26. Inductor 26 is driven with a square wave from excitation signal 24. In the presence of resonant circuit 20, response signal 28 is inductively coupled back to active circuit 18 where a characteristic parameter of response signal 28 can be detected by drive/detection circuit 22. While shown together, it is to be recognized and understood that the drive function and the detection function of drive/detection circuit 22 are completely separable and could be performed by different circuit, even in different locations, perhaps even in different pieces of equipment. Resonant circuit 20 consists of a complementary inductor 30 along with series connected capacitor 32 and resistor 34 form an LRC resonant circuit 20. The values of LRC (including the joint inductance of inductor 26 and inductor 30) in resonant circuit 20 determine the frequency of response signal 28 inductively coupled back to active circuit 18.

Figure 4:
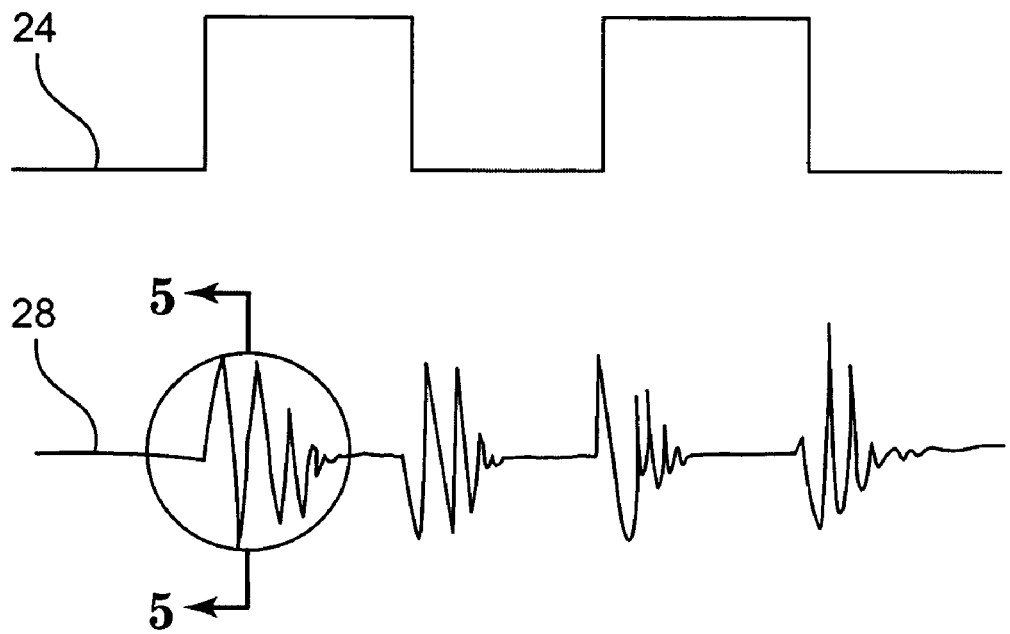
FIG. 4 is a graph illustrating exemplary signals in circuitry used in a hand switch and a surgical handpiece.
Figure 5:
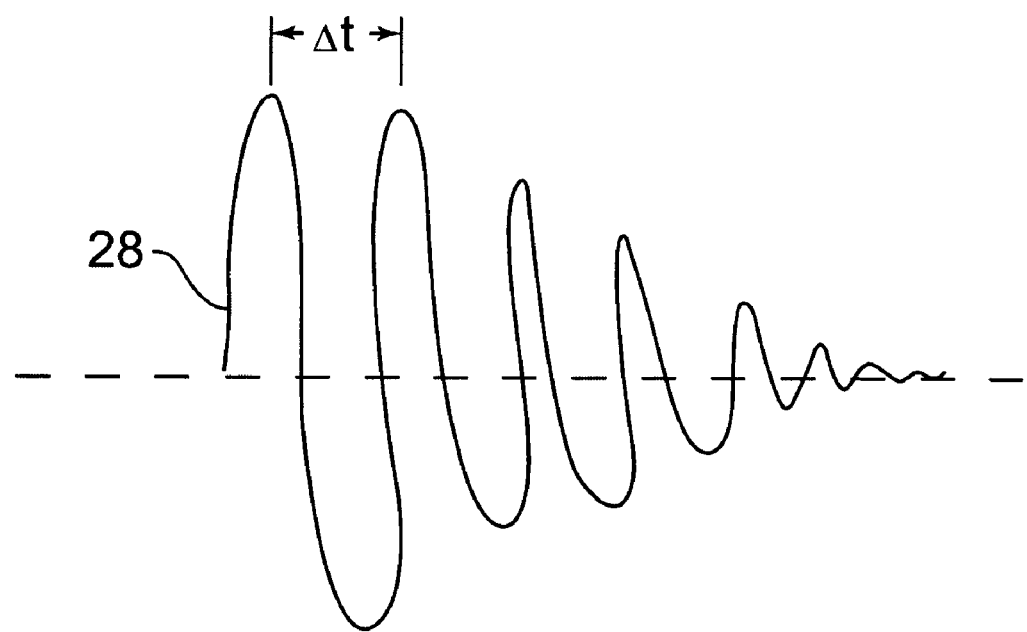
FIG. 5 is an exploded view of a portion of the response signal of FIG. 4.
Figure 6:
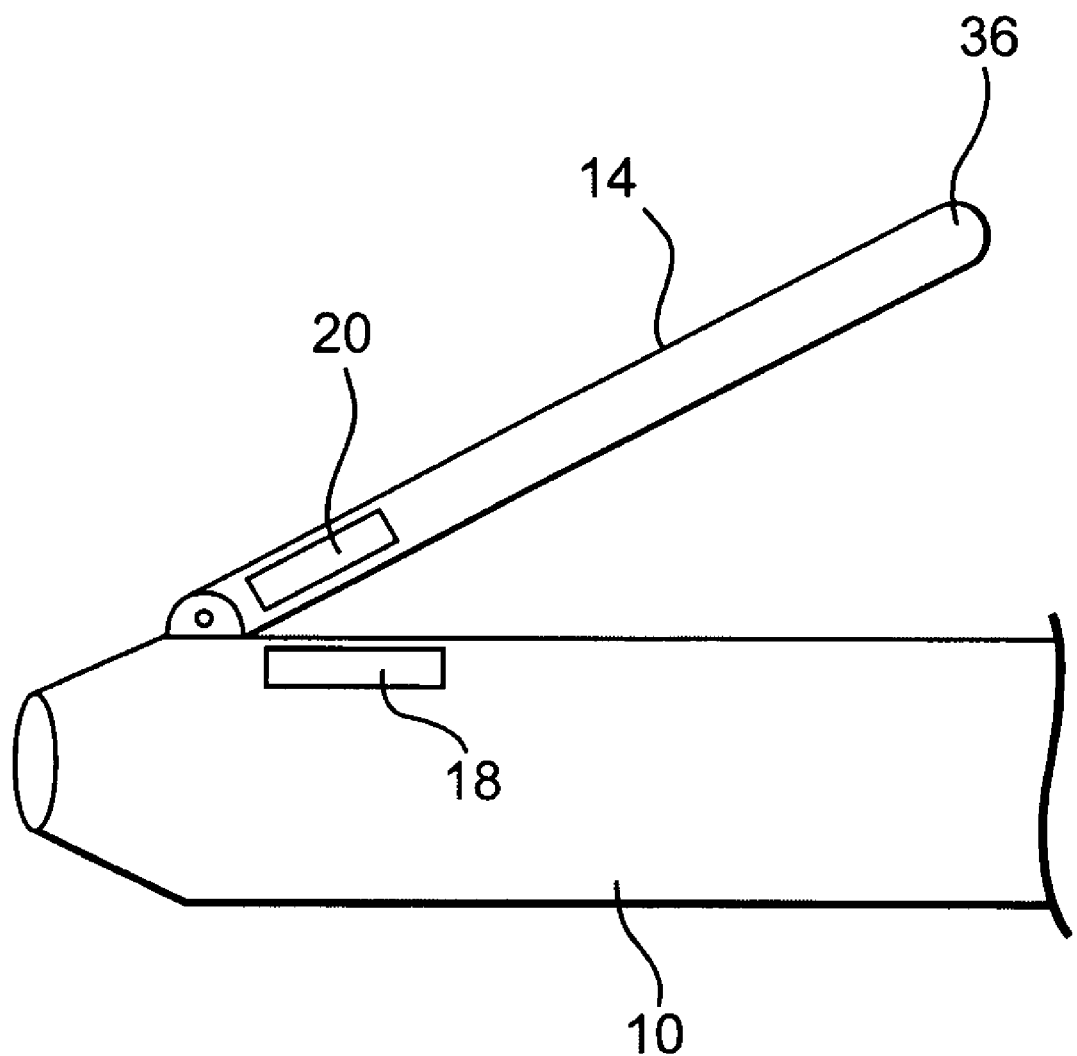
FIG. 6 is an illustration of the use of an embodiment of the present invention in conjunction with a finger trigger.

The characteristics of response signal 28 in response to square wave excitation signal 24 can be seen in FIG. 4. Response signal 28 exhibits a decaying stimulation on each transition of excitation signal 24. An exploded view of one of the decaying stimulations of response signal 28 can be seen in FIG. 5. The period of the decaying stimulation, represented in the figure by Δt, represents a frequency characteristic of the presence of handswitch 14 (or resonant circuit 20) to surgical handpiece 10 (or active circuit 18). Well known, commonly available detection circuitry, such as fast Fourier transform (FFT), can be used to detect the characteristic frequency.

As resonant circuit 20 is brought into closer proximity to active circuit 18, the amplitude of response signal increases. Conversely, when resonant circuit 20 retreats from active circuit 18, the amplitude of response signal 28 decreases. Thus, the amplitude of response signal 28 coupled back to surgical handpiece 10 can be used to sense the relative position of, e.g., a finger trigger 36, on handswitch 14. Thus, the amplitude of response signal 28 can be used for a variable control, e.g., a finger control 36, on handswitch 14.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

The preceding specific embodiments are illustrative of the practice of the invention. It is to be understood, therefore, the other expedients known to those skilled in the art or disclosed herein, may be employed without departing form the invention or the scope of the appended claims. For example, the present invention is not limited to a particular surgical handpiece such as a saw or drill per se, but may find further application as a grinder. The present invention further includes within its scope methods of making and using the invention described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A system, comprising:
    a surgical handpiece adapted to perforin an operation on a patient, said surgical handpiece having a primary circuit being driven by an applied signal;
    a controller operatively coupled to supply operating power to said surgical handpiece;
    a hand switch operatively coupled in conjunction with said surgical handpiece to at least partially control an operation of said surgical handpiece, said switch having a secondary resonant circuit receiving said applied signal from said primary circuit and coupling a response signal back to said primary circuit; and
    detection circuitry, operatively coupled to primary circuit, responsive to a characteristic parameter of said response signal indicative of the presence of said hand switch in proximity of said surgical handpiece.

2. A system as in claim 1 wherein said applied signal is inductively coupled from said secondary resonant circuit back to said primary circuit.

3. A system as in claim 2 wherein said response signal has an amplitude and wherein said detection circuitry detects a position of said hand switch based, at least in part, as a function of said amplitude of said response signal.

4. A system as in claim 1 wherein said characteristic parameter of said response signal comprises a frequency of said response signal.

5. A system as in claim 1 wherein said characteristic parameter of said response signal comprises a time constant of said response signal.

6. A system as in claim 1 wherein said applied signal comprises a square wave.

7. A system as in claim 1 wherein said hand switch activates said surgical handpiece.

8. A system as in claim 1 wherein said hand switch comprises a finger control that modifies an operating characteristic of said surgical handpiece.

9. A system as in claim 1 wherein said hand switch is removable from said surgical handpiece.

10. A system as in claim 1 wherein said applied signal is supplied from said controller.

11. A system as in claim 10 wherein said controller drives said primary circuit.

12. A system as in claim 11 wherein said controller comprises said detection circuitry.

13. A system as in claim 12 wherein said controller comprises a control console.

14. A system as in claim 13 wherein said control console at least partially controls said surgical handpiece.

15. A system as in claim 1 wherein said surgical handpiece comprises a drill.

16. A system as in claim 1 wherein said surgical handpiece comprises a saw.

17. A system, comprising:
    a surgical handpiece adapted to perform an operation on a patient, said surgical handpiece having a primary circuit being driven by an applied signal;
    a controller operatively coupled to supply operating power to said surgical handpiece;
    a hand switch operated by finger control of an operator and operatively coupled in conjunction with said surgical handpiece to at least partially control an operation of said surgical handpiece, said switch having a secondary resonant circuit receiving said applied signal from said primary circuit and inductively coupling a response signal back to said primary circuit; and
    detection circuitry, operatively coupled to primary circuit, responsive to a characteristic parameter of said response signal indicative of the presence of said hand switch in proximity of said surgical handpiece, wherein said response signal has an amplitude and wherein said detection circuitry detects a position of said hand switch based, at least in part, as a function of said amplitude of said response signal.

18. A system as in claim 17 wherein said characteristic parameter of said response signal comprises a frequency of said response signal.

19. A system as in claim 18 wherein said characteristic parameter of said response signal comprises a time constant of said response signal.

20. A system as in claim 19 wherein said applied signal comprises a square wave.

21. A system as in claim 20 wherein said hand switch activates said surgical handpiece.

22. A surgical handpiece, comprising:
   an operable tool adapted to perform an operation on a patient;
   a primary circuit being driven by an applied signal;
   a hand switch operatively coupled in conjunction with said tool to at least partially control an operation of said tool, said switch having a secondary resonant circuit receiving said applied signal from said primary circuit and coupling a response signal back to said primary circuit; and
   detection circuitry, operatively coupled to primary circuit, responsive to a characteristic parameter of said response signal indicative of the presence of said hand switch in proximity of said tool.

23. A surgical handpiece as in claim 22 wherein said applied signal is inductively coupled from said secondary resonant circuit back to said primary circuit.

24. A surgical handpiece as in claim 23 wherein said response signal has an amplitude and wherein said detection circuitry detects a position of said hand switch based, at least in part, as a function of said amplitude of said response signal.

25. A surgical handpiece as in claim 22 wherein said characteristic parameter of said response signal comprises a frequency of said response signal.

26. A surgical handpiece as in claim 22 wherein said characteristic parameter of said response signal comprises a time constant of said response signal.

27. A surgical handpiece as in claim 22 wherein said applied signal comprises a square wave.

28. A surgical handpiece as in claim 22 wherein said hand switch activates said tool.

29. A surgical handpiece as in claim 22 wherein said hand switch comprises a finger control that modifies an operating characteristic of said tool.

30. A surgical handpiece as in claim 22 wherein said hand switch is removable from said tool.

31. A surgical handpiece as in claim 22 wherein said tool comprises a drill.

32. A surgical handpiece as in claim 22 wherein said tool comprises a saw.

33. A surgical handpiece, comprising:
   an operable tool adapted to perforin an operation on a patient;
   a primary circuit being driven by an applied signal; and
   a hand switch operatively coupled in conjunction with said tool to at least partially control an operation of said tool, said switch having a secondary resonant circuit receiving said applied signal from said primary circuit and coupling a response signal back to said primary circuit;
   whereby a characteristic parameter of said response signal may be indicative of the presence of said hand switch in proximity of said tool.

34. A surgical handpiece as in claim 33 wherein said applied signal is inductively coupled from said secondary resonant circuit back to said primary circuit.

35. A surgical handpiece as in claim 34 wherein said response signal has an amplitude and wherein a position of said hand switch may be detected, at least in part, as a function of said amplitude of said response signal.

36. A surgical handpiece as in claim 33 wherein said characteristic parameter of said response signal comprises a frequency of said response signal.

37. A surgical handpiece as in claim 33 wherein said characteristic parameter of said response signal comprises a time constant of said response signal.

38. A surgical handpiece as in claim 33 wherein said applied signal comprises a square wave.

39. A surgical handpiece as in claim 33 wherein said hand switch activates said tool.

40. A surgical handpiece as in claim 33 wherein said hand switch comprises a finger control that modifies an operating characteristic of said tool.

41. A surgical handpiece as in claim 33 wherein said hand switch is removable from said tool.

42. A surgical handpiece as in claim 33 wherein said tool comprises a drill.

43. A surgical handpiece as in claim 33 wherein said tool comprises a saw.

44. A system, comprising:
   a surgical handpiece adapted to perform an operation on a patient, said surgical handpiece having a primary circuit being driven by an applied signal;
   control means, operatively coupled to said surgical handpiece, for supplying operating power to said surgical handpiece;
   a hand switch operatively coupled in conjunction with said surgical handpiece to at least partially control an operation of said surgical handpiece, said switch having a secondary resonant circuit receiving said applied signal from said primary circuit and coupling a response signal back to said primary circuit; and
   detection means, operatively coupled to primary circuit, for detecting a characteristic parameter of said response signal indicative of the presence of said hand switch in proximity of said surgical handpiece.

45. A system, comprising:
   a surgical handpiece adapted to perform an operation on a patient, said surgical handpiece having a primary circuit being driven by an applied signal;
   control means, operatively coupled to said surgical handpiece, for supplying operating power to said surgical handpiece;
   a hand switch operated by finger control of an operator and operatively coupled in conjunction with said surgical handpiece to at least partially control an operation of said surgical handpiece, said switch having a secondary resonant circuit receiving said applied signal from said primary circuit and inductively coupling a response signal back to said primary circuit; and
   detection means, operatively coupled to primary circuit, for detecting a characteristic parameter of said response signal indicative of the presence of said hand switch in proximity of said surgical handpiece, wherein said response signal has an amplitude and wherein said detection means detects a position of said hand switch based, at least in part, as a function of said amplitude of said response signal.

46. A surgical handpiece, comprising:
   an operable tool adapted to perform an operation on a patient;

a primary circuit being driven by an applied signal;

a hand switch operatively coupled in conjunction with said tool to at least partially control an operation of said tool, said switch having a secondary resonant circuit receiving said applied signal from said primary circuit and coupling a response signal back to said primary circuit; and detection means, operatively coupled to primary circuit, for detecting a characteristic parameter of said response signal indicative of the presence of said hand switch in proximity of said tool.

* * * * *